United States Patent
Lee et al.

(10) Patent No.: US 10,457,620 B2
(45) Date of Patent: Oct. 29, 2019

(54) SYSTEM FOR PRODUCING PHENOL AND BISPHENOL A INCLUDING REMOVAL UNIT FOR REMOVING METHANOL AND ACETONE

(71) Applicant: LG CHEM, LTD., Seoul (KR)

(72) Inventors: Sang Beom Lee, Daejeon (KR); Sung Kyu Lee, Daejeon (KR); Joon Ho Shin, Daejeon (KR); Sung Ho Lee, Daejeon (KR); Sa Eun Park, Daejeon (KR); In Yong Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/329,087

(22) PCT Filed: Nov. 28, 2017

(86) PCT No.: PCT/KR2017/013650
§ 371 (c)(1),
(2) Date: Feb. 27, 2019

(87) PCT Pub. No.: WO2018/097690
PCT Pub. Date: May 31, 2018

(65) Prior Publication Data
US 2019/0225567 A1 Jul. 25, 2019

(30) Foreign Application Priority Data
Nov. 28, 2016 (KR) .................. 10-2016-0159071

(51) Int. Cl.
*C07C 37/20* (2006.01)
*C07C 37/74* (2006.01)
(Continued)

(52) U.S. Cl.
CPC .............. *C07C 39/16* (2013.01); *B01D 3/32* (2013.01); *C07C 37/08* (2013.01); *C07C 37/20* (2013.01);
(Continued)

(58) Field of Classification Search
CPC ......... C07C 37/00; C07C 37/11; C07C 37/20; C07C 37/68; C07C 37/70; C07C 37/74;
(Continued)

(56) References Cited

U.S. PATENT DOCUMENTS 7,888,537 B2 * 2/2011 Schmidt .................. B01J 29/06
568/385
2006/0211893 A1 * 9/2006 Koga ....................... C07C 37/20
568/728
(Continued)

FOREIGN PATENT DOCUMENTS

JP 2006036668 A * 2/2006
KR 20130019667 A * 2/2013
WO WO-2013154147 A1 * 10/2013 ............. C07C 37/74

OTHER PUBLICATIONS

Machine translation of KR 20130019667 A, which was published Feb. 27, 2013. (Year: 2013).*
(Continued)

*Primary Examiner* — Natasha E Young
(74) *Attorney, Agent, or Firm* — Dentons US LLP (57) ABSTRACT

A system for producing phenol and bisphenol A comprising: a first production unit for producing phenol comprising a decomposition reaction unit and a purification unit; a second production unit for producing bisphenol A comprising a reaction unit and a concentration unit; and a removal unit for removing methanol and acetone during the production of phenol and bisphenol A. The removal unit includes a removal column comprising an overhead purge part, a
(Continued)

bottom recirculation part and a supply part. The supply part comprises a purification unit discharge part to supply methanol, acetone, and water discharged from the purification unit to the removal column and a concentration unit discharge part to supply phenol, acetone, and water discharged from the concentration unit to the removal column, and is provided to the midsection of the removal column.

7 Claims, 5 Drawing Sheets

(51) Int. Cl.
    *C07C 37/88*     (2006.01)
    *C07C 39/04*     (2006.01)
    *C07C 39/16*     (2006.01)
    *B01D 3/32*     (2006.01)
    *C07C 37/08*     (2006.01)
    *C07C 37/68*     (2006.01)
    *C07C 37/70*     (2006.01)
    *C07C 37/86*     (2006.01)

(52) U.S. Cl.
    CPC .............. *C07C 37/68* (2013.01); *C07C 37/70* (2013.01); *C07C 37/74* (2013.01); *C07C 37/86* (2013.01); *C07C 37/88* (2013.01); *C07C 39/04* (2013.01)

(58) Field of Classification Search
    CPC ......... C07C 37/88; C07C 39/00; C07C 39/02; C07C 39/04; C07C 39/12; C07C 39/15; C07C 39/16
    See application file for complete search history.

(56) References Cited

U.S. PATENT DOCUMENTS

| | | |
|---|---|---|
| 2009/0221858 A1 | 9/2009 | Evitt et al. |
| 2011/0137087 A1 | 6/2011 | Young et al. |
| 2013/0068609 A1 | 3/2013 | Bhargava et al. |
| 2013/0072723 A1 | 3/2013 | Wilks et al. |
| 2016/0159716 A1 | 6/2016 | Park et al. |

OTHER PUBLICATIONS

Machine translation of JP 2006-036668 A, which was published Feb. 9, 2006. (Year: 2006).*

* cited by examiner

SYSTEM FOR PRODUCING PHENOL AND BISPHENOL A INCLUDING REMOVAL UNIT FOR REMOVING METHANOL AND ACETONE

CROSS-REFERENCE TO RELATED APPLICATION

This application is a National Stage Entry of International Application No. PCT/KR2017/013650, now WO 2018/097690, filed on Nov. 28, 2017, and claims the benefit of and priority to Korean Application No. 10-2016-0159071, filed on Nov. 28, 2016, all of which are hereby incorporated by reference in their entirety for all purposes as if fully set forth herein.

TECHNICAL FIELD

The present invention relates to a removal unit of methanol and acetone provided in a system including a production system of bisphenol A and a production system of phenol, and to a production system of phenol and bisphenol A including the same.

BACKGROUND ART

Bisphenol A is produced by reacting excess phenol with acetone in the presence of an acid catalyst. In order to obtain high-purity bisphenol A from this reaction product, low boiling point materials including water are removed therefrom, and crystallization is performed to precipitate a solid adduct crystal of bisphenol A and phenol. After the slurry containing the solid adduct is subjected to solid-liquid separation, phenol is removed from the recovered solid adduct to obtain bisphenol A.

Phenol is produced using cumene as a raw material, and cumene is oxidized using a gas containing oxygen to form cumene hydroperoxide, which is then decomposed under an acidic catalyst to produce phenol and acetone.

Figure 1:
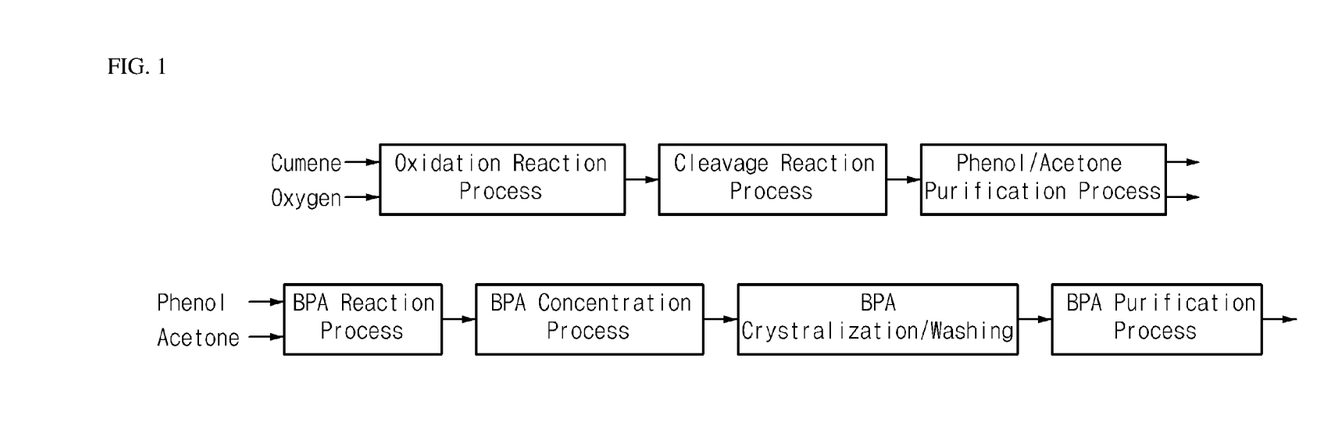
FIG. 1 is a simplified schematic diagram illustrating a production system of phenol and a production system of bisphenol A.

FIG. 1 is a simplified schematic diagram illustrating the production process of bisphenol A and the production process of phenol. Referring to FIG. 1, after an oxidization reaction using cumene and oxygen as raw materials is performed, a reaction in which cumene hydroperoxide as a cumene oxide is decomposed is performed. Then, through a purification process, phenol and acetone are produced as a product thereof, and alpha-methylstyrene is additionally produced. Also, bisphenol A is produced by reacting phenol with acetone, and the bisphenol A produced therefrom is concentrated through the removal of low boiling point materials, and then crystallized, washed, and purified to produce bisphenol A.

Regarding such a production process of phenol and a production process of bisphenol A, since the products of the production process of phenol are used as raw materials for a reaction in the production process of bisphenol A, there are typically two processes in a single factory.

Meanwhile, the production process of bisphenol A has a problem in that methanol included as an impurity in acetone which is a raw material acts as a catalyst poison in a reactor, thereby shortening the lifespan of a catalyst. To solve this problem, typically, a distillation tower for removing methanol from the raw material of acetone is separately installed to perform a separation process. However, there is a problem in that the separation between acetone and methanol using distillation requires a large number of stages so that the energy consumption is high.

Also, in the case in which high-purity bisphenol A cannot be obtained due to a large amount of side reaction materials produced, the quality of a bisphenol A product is deteriorated, and in particular, there is a problem in that color at high temperature melting, which is an important factor of a bisphenol A product, cannot be obtained at a desired level.

In relation to this, in order to increase the production amount of bisphenol A, the amount of acetone to be introduced should be increased. However, due to a lowered ratio of phenol to acetone, that is, since the ratio of phenol is relatively lowered, a large amount of side reaction materials are produced. To overcome this problem, the amount of phenol to be introduced is also increased to prevent the relative content reduction of phenol to acetone. However, due to an increase in residence time, the conversion rate of acetone is maintained low.

In the case in which the content of acetone is increased as described above, not only there is a problem in that methanol included as an impurity in acetone acts as a catalyst poison in a reactor, but also a problem in that the amount of unconverted acetone is increased so that a large amount thereof cannot be recovered in a recovery process of acetone through a dehydration column, and therefore, is introduced into a dephenolation process together with water which is a side reaction material of the reaction. The acetone introduced into the dephenolation process may cause a problem of greatly deteriorating a treatment process of wastewater containing phenol, the process included in the dephenolation process operated through extraction.

Therefore, due to a problem caused by acetone, there is a problem in that the production process of bisphenol A is limited by the capacity of a dehydration column provided in the process of recovering acetone.

That is, there is a need for the development of a technology for efficiently removing methanol included in acetone produced in the production process of phenol. There is also a need for the development of a technology capable of, by providing acetone not including methanol for the production process of bisphenol A, improving the lifespan of a catalyst, and at the same time, increasing productivity by improving the selectivity of bisphenol A.

PRIOR ART DOCUMENT

Patent Document

Korean Patent Laid-Open Publication No. 10-2015-0008005

DISCLOSURE OF THE INVENTION

Technical Problem

The present invention has been devised to solve the above problems. An aspect of the present invention provides a removal unit of methanol and acetone, and a production system of phenol and bisphenol A including the same, which are capable of removing methanol, which is difficult to separate, together with acetone by applying a separate removal unit in a system provided with a production system of phenol and a production system of bisphenol A, and of freely controlling the conversion rate of acetone without being limited by the capacity of a dehydration column even when the conversion rate of acetone is lowered to improve the selectivity of bisphenol A.

Technical Solution

In order to solve the above problems, an aspect of the present invention provides a removal unit of methanol and acetone provided in a system including a production system of phenol having a decomposition reaction unit and a purification unit, and a production system of bisphenol A having a reaction unit and a concentration unit, the removal unit comprising, a removal column; a supply part provided in the midsection of the removal column; an overhead purge part in which methanol and acetone are removed; and a bottom recirculation part recirculated to the purification unit, wherein the supply part includes a purification unit discharge part in which methanol, acetone, and water are included, and a concentration unit discharge part in which phenol, acetone, and water are included.

Another aspect of the present invention provides a production system of phenol and bisphenol A including the removal unit of methanol and acetone described above.

In an exemplary embodiment, this application is directed to system for producing phenol and bisphenol A comprising: a first production unit for producing phenol comprising a decomposition reaction unit and a purification unit; a second production unit for producing bisphenol A comprising a reaction unit and a concentration unit; and a removal unit for removing methanol and acetone during the production of phenol and bisphenol A, the removal unit comprising: a removal column comprising an overhead purge part, a bottom recirculation part and a supply part. The supply part comprises a purification unit discharge part to supply methanol, acetone, and water discharged from the purification unit to the removal column and a concentration unit discharge part to supply phenol, acetone, and water discharged from the concentration unit to the removal column, and the supply part is provided to the midsection of the removal column. The overhead purge part removes methanol and acetone from the removal column, and the bottom recirculation part recirculates phenol, water, and trace amounts of methanol and acetone to the purification unit.

In another exemplary embodiment, the purification unit comprises: a first column for separating a reaction product discharged from the decomposition reaction unit into an acetone-rich fraction and a phenol-rich fraction; a second column connected to an acetone-rich discharge line for purifying the acetone-rich fraction discharged from a top of the first column; and a separator connected to the acetone removal discharge line for separating an acetone removal fraction discharged from the bottom of the second column into an aqueous layer fraction comprising methanol, acetone and water, and an organic layer fraction. The purification unit discharge part comprises an aqueous layer discharge line through which the aqueous layer fraction is discharged from the separator.

In another exemplary embodiment, the concentration unit comprises: a dehydration column for removing unreacted acetone and water from a reaction product discharged from the reaction unit; and an acetone recovery column connected to an unreacted acetone discharge line discharged from an upper end of the dehydration column for recovering acetone by removing acetone from the water-rich fraction. The concentration unit discharge part comprises a water-rich discharge line through which a water-rich fraction comprising phenol, acetone, and water is discharged from the acetone recovery column.

In another exemplary embodiment, the bottom recirculation part recirculated to the purification unit comprises methanol in an amount of 100 ppm or less based on a total weight of flow.

In another exemplary embodiment, a reaction in which phenol and acetone are produced from cumene oxide and an acid solution is performed in the decomposition reaction unit.

In another exemplary embodiment, the purification unit further comprises a neutralizer at a front end part of the first column, and the neutralizer neutralizes the reaction product discharged from the decomposition reaction unit.

In another exemplary embodiment, a reaction in which bisphenol A and water are produced is performed in the reaction unit.

Advantageous Effects

According to a removal unit of methanol and acetone, and a production system of phenol and bisphenol A including the same according to an embodiment of the present invention, by applying a separate removal unit in a system provided with a production system of phenol and a production system of bisphenol A, methanol, which is difficult to separate, is removed together with acetone, and even when the conversion rate of acetone is lowered to improve the selectivity of bisphenol A, the conversion rate of acetone may be freely controlled without being limited by the capacity of a dehydration column so that it is possible to improve the lifespan of a catalyst, and to increase the productivity of bisphenol A due to the improvement of the selectivity of bisphenol A.

MODE FOR CARRYING OUT THE INVENTION

Hereinafter, the present invention will be described in more detail to allow for a clearer understanding of the present invention. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

According to an embodiment of the present invention, provided is a removal unit of methanol and acetone, the unit provided in a system including a production system of phenol having a decomposition reaction unit and a purification unit, and a production system of bisphenol A having a reaction unit and a concentration unit.

The removal unit includes a removal column, a supply part provided in the midsection of the removal column, an overhead purge part in which methanol and acetone are removed, and a bottom recirculation part in which the removed methanol and acetone are recirculated to a purification unit, wherein the supply part includes a purification unit discharge part in which methanol, acetone, and water are included, and a concentration unit discharge part in which phenol, acetone, and water are included.

Hereinafter, a removal unit of methanol and acetone, and a production system of phenol and bisphenol A including the same according to the present invention will be described with reference to the accompanying drawings. The accompanying drawings which are included to provide a further understanding of the present invention are merely illustrative of the embodiment according to the present invention. They are not to be construed as limiting the scope of the present invention, but should be construed in accordance with the technical concept of the present invention.

Referring to FIG. 1, schematic process sequences of a production system of phenol and a production system of bisphenol A are illustrated. As described above, in the production system of phenol, after an oxidization reaction using cumene and oxygen as raw materials is performed, a reaction in which cumene hydroperoxide as a cumene oxide is decomposed is performed. Then, through a purification process, phenol and acetone are produced as products thereof, and alpha-methylstyrene is additionally produced.

Also, bisphenol A is produced by reacting phenol with acetone, and the bisphenol A produced therefrom is concentrated through the removal of low boiling point materials, and then crystallized, washed, and purified to produce bisphenol A. Phenol and acetone which are raw materials supplied to the production system of bisphenol A may be generally derived from the production system of phenol.

Purification Unit in the Production System of Phenol

Figure 2:
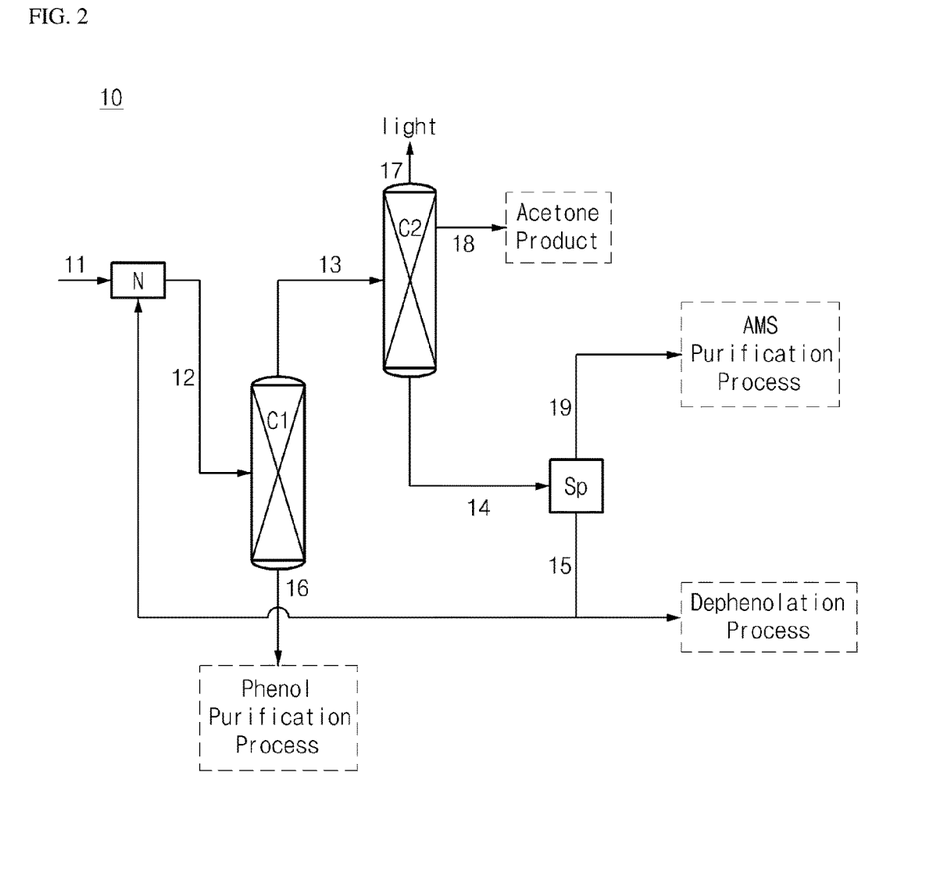
FIG. 2 is a process flowchart illustrating an example of a purification unit in a production system of phenol.

FIG. 2 illustrates an example of a purification unit 10 in the production system of phenol and exemplarily describes the purification unit 10 existing in the production system of phenol.

The purification unit 10 may be connected to a flow in which a reaction product discharged from a decomposition reaction unit (not shown) is introduced, and the flow may be one flown into through a purification unit inflow line 11. The purification unit 10 may play roles in separating a product of a reaction, the reaction in which cumene hydroperoxide is decomposed, into a phenol-rich fraction and an acetone-rich fraction and purifying each of them, and separating an alpha-methylstyrene fraction and purifying the same.

The purification unit 10 may include a first column C1 for separating the reaction product discharged from the decomposition reaction unit into an acetone-rich fraction and a phenol-rich fraction; a second column C2 connected to an acetone-rich discharge line 13, for purifying the acetone-rich fraction discharged from the overhead of the first column C1; and a separator Sp connected to an acetone removal discharge line 14, for separating an acetone removal fraction discharged from the bottom of the second column C2 into an aqueous layer fraction and an organic layer fraction.

The first column C1 may be a distillation column separating the phenol-rich fraction and the acetone-rich fraction, and may have a phenol-rich discharge line 16 through which the phenol-rich fraction flows at the bottom thereof, and have the acetone-rich discharge line 13 through which the acetone-rich fraction flows at the overhead thereof.

In addition, before the reaction product discharged from the decomposition reaction unit is introduced into the first column C1, a product neutralized by passing through a neutralizer N may be introduced. Thus, a first column inflow line 12 introduced into the first column C1 may be one through which a product of decomposition reaction neutralized flows.

The phenol-rich discharge line 16 discharged from the bottom of the first column C1 may be introduced into a purification part of phenol including one or more columns, and through the process, a purified high-purity phenol product may be produced.

To the second column C2, the acetone-rich discharge line 13 discharged from the overhead of the first column C1 may be introduced. The second column C2 may serve a role of an acetone product column, from the overhead of which low boiling point materials may be removed through a low-boiling point substance removal line 17, and in the midsection of the second column C2, a flow of acetone product may flow through an acetone discharge line 18, and to the flow of acetone product, a purification process for improving purity may be selectively applied when needed.

Through the acetone removal discharge line 14 provided at the bottom of the second column C2, a flow from which most of acetone is removed and containing alpha-methylstyrene as the main component may flow, and the flow may be introduced into the separator Sp to be separated into the aqueous layer fraction and the organic layer fraction.

That is, in the separator Sp, an operation of separating the flow into an organic layer and an aqueous layer may be performed using layer separation. In the organic layer, alpha-methylstyrene is included as the main component and provided through an organic layer discharge line 19 to a purification part which produces a product using alpha-methylstyrene. Through the aqueous layer discharge line 15, an aqueous layer fraction having water, methanol, and acetone as main components is discharged and a portion thereof may be used for recirculation and the remainder thereof may be introduced to a dephenolation process.

Concentration Unit in the Production System of Bisphenol A

Figure 3:
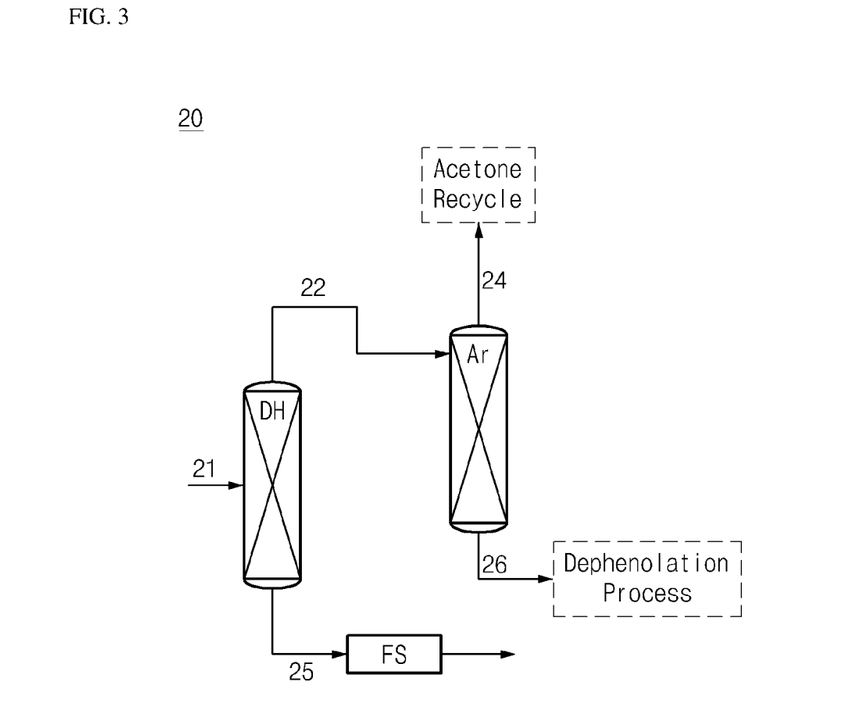
FIG. 3 is a process flowchart illustrating an example of a concentration unit in a production system of bisphenol A.

FIG. 3 illustrates an example of a concentration unit 20 in the production system of bisphenol A, exemplarily describing the concentration unit 20 in the production system of bisphenol A.

The concentration unit 20 may serve a role of concentrating bisphenol A by removing impurities from a reaction product discharged from a reaction unit of bisphenol A.

Stoichiometrically, the production of bisphenol A consumes 2 mole of phenol and 1 mole of acetone to yield 1 mole of bisphenol A and 1 mole of water. However, industrially, bisphenol A is produced by reacting excess phenol with acetone in the presence of an acid catalyst. In order to obtain high-purity bisphenol A from this reaction product, the reaction product is concentrated, and then crystalized to precipitate a crystalized adduct of bisphenol A and phenol. After the obtained crystal slurry is subjected to solid-liquid separation, phenol is removed from the recovered crystal to obtain bisphenol A.

In an acid-catalyzed reaction of phenol and acetone, the ratio of phenol to acetone may be, for example, 5:1, 7:1, 8:1, or 9:1. The reaction is typically performed continuously, and may be generally performed at a temperature of 45° C. and 110° C., 50° C. and 105° C., 55° C. and 100° C., or 58° C. and 90° C. For example, as the acid catalyst, strong inorganic acid, for example, a homogeneous and heterogeneous acid such as hydrochloric acid or sulfuric acid, or a Brønsted or Lewis acid thereof may be used. Also, a cation exchange resin or zeolite, and the like may be used.

In addition, a gel-like or porous sulfonated crosslinked polystyrene resin (acid ion exchanger) containing divinylbenzene as a crosslinking agent may be desirably used. In addition to the catalyst, a thiol may be used as a co-catalyst, and for example, methyl mercaptan may be used. As the main reactor, for example, a vertical fixed phase reactor or a mobile phase reactor filled with a sulfonic acid-type cation exchange resin catalyst may be used, and a reaction may be continuously performed by circulating a phenol raw material and an acetone raw material to the reactor. After performing the reaction for a certain period of time, the operation may be stopped and washing or exchanging of a deteriorated catalyst may be performed.

In the reaction of phenol and acetone under the acid catalyst, in addition to unreacted phenol and acetone, a reaction product which is a mixture preferentially containing bisphenol A and water may be formed. Also, as impurities, typical byproducts of a condensation reaction may be generated, and additional subcomponents, such as anisole, mesh oxide, mesitylene, and diacetone alcohol may be formed as a result of the natural condensation of acetone and the reaction with impurities in the raw materials. Not only secondary products such as water but also unreacted raw materials such as phenol and acetone may be separated by an appropriate method due to the detrimental effect thereof on the suitability of bisphenol A for preparing a polymer.

As described above, the product from the reaction unit, the product including unreacted raw materials, impurities, and reaction products of impurities together with the product of the reaction may be introduced to the concentration unit 20 through the dehydration column inflow line 21.

The concentration unit 20 may include a dehydration column DH for removing unreacted acetone and water from the reaction product discharged from the reaction unit; and an acetone recovery column Ar connected to an unreacted acetone discharge line 22 discharged from an upper end of the dehydration column DH, for recovering acetone by removing the acetone from a water-rich fraction.

The dehydration column DH may be a distillation device capable of removing a low boiling point material. A flow of a reaction product of bisphenol A may be introduced to the dehydration column DH through the dehydration column inflow line 21, and the dehydration column DH may remove a material having a boiling point lower than that of bisphenol A including water from the reaction product by vaporization. The lower internal temperature of the dehydration column DH may be controlled to be 150° C. to 200° C., 155° C. to 195° C., 160° C. to 190° C., or 165° C. to 186° C. The internal pressure of the dehydration column DH may be controlled to be 200 mmHg to 760 mmHg, 300 mmHg to 730 mmHg, 400 mmHg to 700 mmHg, or 450 mmHg to 680 mmHg. By controlling the internal temperature and the internal pressure as described above, a low boiling point material having a boiling point lower than that of phenol and bisphenol A may be efficiently removed. In order to increase the temperature of the dehydration column DH, an external heat source (not shown) may be supplied. Generally, the external heat source may be supplied through steam.

From the dehydration column DH, a flow in which a co-catalyst or byproducts are included together with acetone, phenol, and excess water, may be discharged through the unreacted acetone discharge line 22, and then may be introduced to the acetone recovery column Ar. The acetone recovery column Ar is for removing or recovering acetone (including a co-catalyst in some cases), and from the acetone recovery column Ar, materials which have been subjected to gas-liquid separation may be discharged through the overhead or the bottom. Through the top, a flow including acetone as a main component together with a co-catalyst such as mercaptan may be discharged through an acetone recovery column overhead discharge line 24, and in some cases, may be used again through recirculation. Through the bottom, a flow including water as a main component together with acetone with phenol may be discharged through a water-rich discharge line 26, which may be introduced into the dephenolation process.

Meanwhile, through the bottom of the dehydration column DH, a flow including phenol and bisphenol A as main components may flow through a dehydration column bottom discharge line 25, and through the top, a flow including acetone as a main component as a low boiling point component may flow through the acetone discharge line 22. The flow including acetone discharged from the overhead may go through the acetone recovery column Ar and be discharged from the top of the column to be used for recirculation. The flow including phenol and bisphenol A as main components and discharged through the bottom, may be discharged through a flash unit FS as a flow of concentrated bisphenol A.

Removal Unit of Methanol and Acetone

A removal unit according to an embodiment of the present invention may be provided in a system including the production system of phenol and the production system of bisphenol A described above.

Specifically, the removal unit is provided in a system including a production system of phenol having a decomposition reaction unit and a purification unit, and a production system of bisphenol A having a reaction unit and a concentration unit.

The removal unit includes a removal column; a supply part provided in the midsection of the removal column; an overhead purge part in which methanol and acetone are removed; and a bottom recirculation part recirculated to a purification unit, wherein the supply part includes a purification unit discharge part in which methanol, acetone, and water are included, and a concentration unit discharge part in which phenol, acetone, and water are included.

Figure 4:
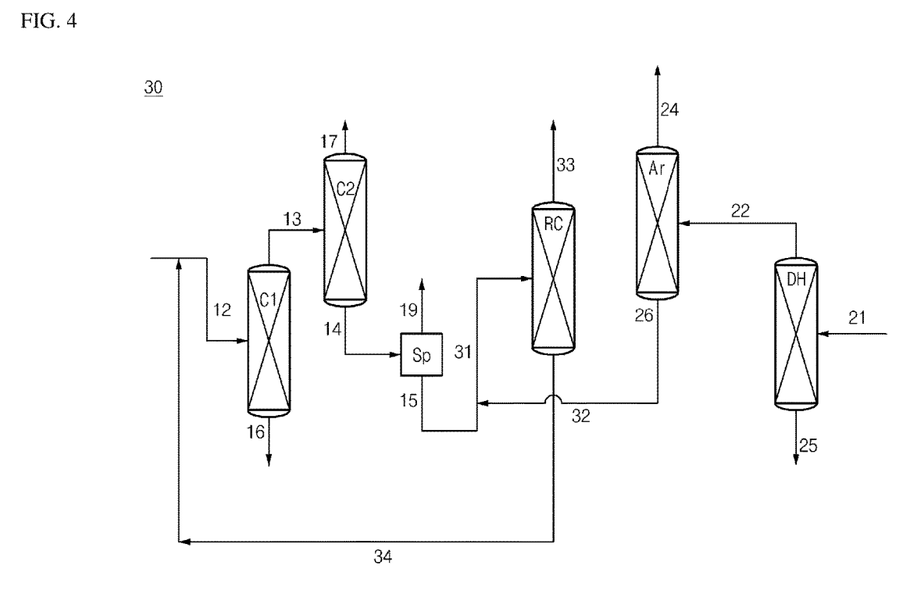
FIG. 4 is a process flowchart illustrating an example of a removal unit of methanol and acetone according to the present invention.

FIG. 4 illustrates an example of a removal unit of methanol and acetone according to an embodiment of the present invention, and the removal unit will be described with reference to FIG. 4.

To the removal column RC, a purification unit discharge part 31 and a concentration unit discharge part 32 discharged from the purification unit and the concentration unit may be introduced, and a supply part of the removal column RC may include these discharge parts. The supply part includes the purification unit discharge part 31 and the concentration unit discharge part 32, and may be configured in various ways such that the two flows may be connected through a piping line, or may be introduced into the removal column RC through another inlet, and the like.

Specifically, through the purification unit discharge part 31, a flow including sodium phenoxide, methanol, acetone, and water flows. In the flow, water is the main component, and may be included in an amount of 50 wt % or more based on the total weight. The flow may be derived from the aqueous layer discharge line 15 (not shown in FIG. 4) of the separator Sp of the purification unit. Also, through the concentration unit discharge part 32, a flow including phenol, methanol, acetone, and water flows. In this flow, water also may be the main component and may be included in an amount of 50 wt % based on the total weight. The flow may be derived from the water-rich discharge line 26 (not shown in FIG. 4) of the acetone recovery column Ar of the concentration unit.

The removal column RC is a column for removing methanol and acetone. Through the overhead of the removal column RC, a flow in which methanol and acetone are purged may flow to an overhead purge part 33. The flow may be purged, or may be supplied to a process for producing isopropyl alcohol using the hydrogenation reaction of acetone, and the like such that the recycling thereof may be appropriately considered.

In addition, from the bottom of the removal column RC, a flow in which methanol and acetone are removed and phenol and water are main components may flow through a bottom recirculation part 34, and hydroxy acetone, sodium hydroxide and the like may be contained in a trace amount therein. Also, an ultra trace amount of unseparated methanol may flow therethough. The flow may be recirculated to the purification unit, or may be introduced to a front end of a neutralizer (not shown), or may be introduced to the first column inflow line 12. The flow of the bottom recirculation part 34 may be separated into the phenol-rich fraction and the acetone-rich fraction in the first column C1 to benefit from the reuse of phenol.

In the bottom recirculation part, the content of methanol may be about 100 ppm or less by weight, and removal of such methanol may prevent the accumulation of methanol in the system. Also, in the bottom recirculation part, acetone may be almost nonexistent.

As described above, methanol may act as a catalyst poison in a reactor, which may be included in the reaction unit of bisphenol A, and shorten the lifespan of a catalyst. Also, in the case in which acetone, which is included in a signification amount in a product flow due to a lowered conversion rate of acetone to improve the selectivity of bisphenol A, is introduced to the dephenolation process, there is a concern that the efficiency of the extraction operation may be sharply decreased. Further, it is very difficult to separate methanol included as an impurity in acetone produced in the production system of phenol, from acetone. For the separation, a considerable number of operations are required, and thus, energy consumption thereof may be considerable.

The removal unit according to the present invention may considerably decrease the amount of methanol in a flow recirculated to the purification unit of phenol by removing methanol and acetone through the removal unit. As a result, methanol in acetone used for the production of bisphenol A in the production system of bisphenol A may be reduced, and the absolute amount of acetone introduced into the dephenolation process may be reduced, thereby solve the problems described above. Accordingly, the improvement of productivity may be expected according to the lifespan improvement of a catalyst and the increase in the selectivity of bisphenol A.

Specifically, by applying the removal unit as a device in which methanol and acetone can be removed, it is possible to freely control the conversion rate of acetone regardless of the capacity of the dehydration column in order to improve the selectivity of bisphenol A. Accordingly, the improvement of productivity of bisphenol A is expected, and the lifespan of a reaction catalyst may be improved due to the removal of methanol so that a synergetic effect with the selectivity improvement may be obtained. Also, since there is no need to install a separate column for removing methanol, energy savings may be also expected.

As described above, it is quite difficult to separate methanol and acetone. However, when the separation operation is performed with water as in the present invention, the separation may be considerably easy. That is why a flow including water as a main component is simultaneously introduced into the removal column RC. By supplying the aqueous layer fraction flowing through the purification unit discharge part 31 and the water-rich fraction flowing through the concentration unit discharge line 32, ultimately, it is possible reduce the amount of methanol accumulated in the system.

The description of how a flow becomes a flow flowing in the purification unit discharge part 31 is the same as the description of the purification unit 10 in the production system of phenol described above. The description of how a flow becomes a flow flowing in the concentration unit discharge part 32 is the same as the description of the concentration unit 20 in the production system of bisphenol A described above.

Figure 5:
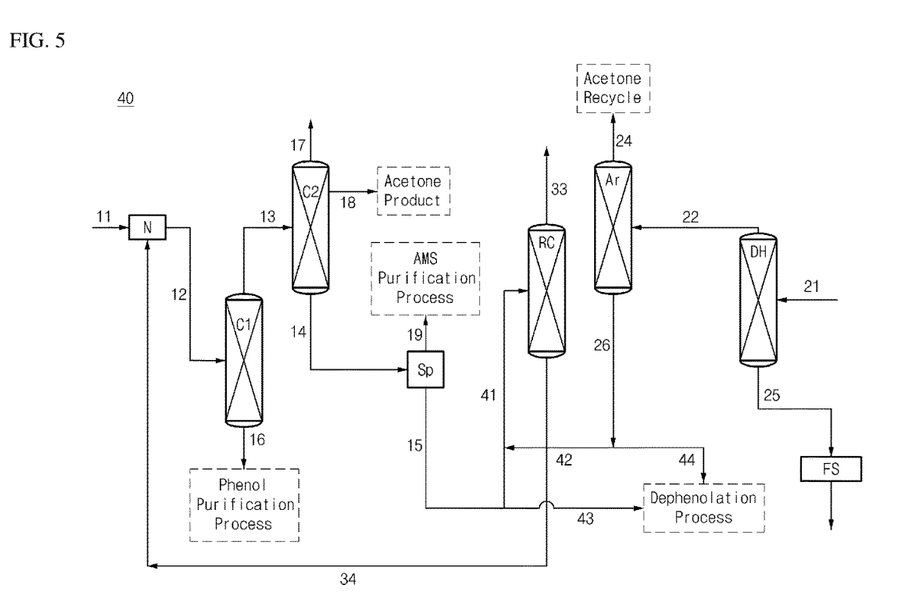
FIG. 5 is a process flow chart illustrating an example of a removal unit of methanol and acetone according to the present invention in more detail.

FIG. 5 illustrates an example of a removal unit according to an embodiment of the present invention in more detail and the removal unit will be described with reference to FIGS. 4 and 5.

In the removal unit 30, as shown in FIG. 4, the supply part of the removal column RC includes the purification unit discharge part 31 and the concentration unit discharge part 32. Referring to FIG. 5, the purification unit discharge part 31 (not shown in FIG. 5) may include the aqueous discharge line 15 through which an aqueous layer is discharged from the separation SP of the purification unit 10, and may be derived therefrom. The flow flowing through the aqueous discharge line 15 may be divided so that a portion of the flow may flow through a first supply line 41 which can be seen as the same line as the purification unit discharge part 31, and the remainder may flow through a first dephenolation process inflow line 43 which is introduced to the dephanolation process.

In the case in which the flow is divided as described above, a flow flowing through the first supply line 41 may flow being 30 to 95 wt % based on the total volume of the aqueous layer discharge line 15. If the flow flowing through the first supply line 41 is less than 30 wt %, the amount of methanol, acetone, hydroxy acetone is increased so that a problem may occur in the extraction operation.

In addition, the concentration unit discharge part 32 (not shown in FIG. 5) may include the water-rich discharge line 26 through which a water-rich fraction is discharged from the acetone recovery column Ar of the concentration unit 20, and may be derived therefrom. The flow flowing through the water-rich discharge line 26 may be divided so that a portion of the flow may flow through a second supply line 42 which can be seen as the same line as the concentration unit discharge part 32, and the remainder may flow through a second dephenolation process inflow line 44 which is introduced to the dephanolation process.

In the case in which the flow is divided as described above, a flow flowing through the first supply line 41 may flow being 5 to 100 wt % based on the total volume of the water-rich discharge line 26. If the flow flowing through the second supply line 42 is less than 5 wt %, the amount of acetone is increased so that a problem may occur in the extraction operation.

However, the amount of flows flowing through the first supply line 41 and the second supply line 42 respectively may be appropriately controlled, is not greatly limited to the ranges described above, and may be selectively adjusted by a person skilled in the art according to circumstances.

The detailed descriptions of the purification unit 10 and the concentration unit 20 are the same as those described above, and therefore, the descriptions thereof will be omitted All of the units described above may include a heat exchanger at the front and/or rear of the column, and may further include reflux means such as a condenser or a reboiler. Although not illustrated in the accompanying drawings, additional devices for improving the energy efficiency and productivity of the process may be further included.

Production System of Phenol and Bisphenol A

According to an embodiment of the present invention, provided is a production system of phenol and bisphenol A, and the production system includes the removal unit described above.

A purification unit of phenol and a concentration unit of bisphenol A included in the production system of phenol and bisphenol A are the same as described above, and a removal unit is also the same as described above. As for other units, for example, an oxidization reaction unit and a decomposition reaction unit may be included in the production system of phenol, and a reaction unit, a crystallization unit, and a purification unit may be included in the production system of bisphenol A.

By including the removal unit described above in the production system of phenol and bisphenol A, the improvement of productivity due to the improvement of selectivity of bisphenol A may be expected and the lifespan of a catalyst may be improved by preventing the accumulation of methanol in the system.

EXAMPLE

Hereinafter, the present invention will be described in detail with reference to examples. However, the embodiments according to the present invention may be modified into various other forms, and the scope of the present invention should not be construed as being limited to the embodiments described below. Embodiments of the present invention are provided to more fully describe the present invention to those skilled in the art.

In the following Examples 1 and 2, a system including a removal unit according to the present invention is simulated using a commercial process simulation program ASPEN PLUS. The distillation tower used in the simulation was operated under the conditions of the theoretical stage number of 28 and the pressure of an atmospheric pressure level.

Example 1

An aqueous layer fraction of 6,630 kg/hr flowing through the first supply line 41 which is the purification unit discharge part 31 included in the production system of phenol and derived from the aqueous layer discharge line 15, and a water-rich fraction of 2,452.2 kg/hr flowing through the second supply line 42 which is the concentration unit discharge part 32 included in the production system of bisphenol A and derived from the water-rich discharge line 26 are introduced into the removal column RC. The ratio of the compositions in each flow is shown in Table 1 below.

Example 2

Except that a water-rich fraction of 2,571.0 kg/hr flowing through the second supply line 42 which is the concentration unit discharge part 32 included in the production system of bisphenol A and derived from the water-rich discharge line 26 was introduced into the removal column RC, the same procedure as in Example 1 was performed. The ratio of the components in each flow is shown in Table 1 below.

TABLE 1

| Line | Component | Example 1 | Example 2 |
|---|---|---|---|
| $1^{st}$ line from purification unit (aqueous layer fraction) | Sodium phenoxide (wt %) | 1.40 | 1.40 |
| | Acetone (wt %) | 0.11 | 0.11 |
| | Methanol (wt %) | 0.15 | 0.15 |
| | Propanol (wt %) | 0.09 | 0.09 |
| | Methyl ethyl ketone (wt %) | 0.02 | 0.02 |
| | Hydroxy acetone (wt %) | 0.15 | 0.15 |
| | MO (wt %) | 0.02 | 0.02 |
| | NaOH (wt %) | 0.34 | 0.34 |
| | Water (wt %) | balance | balance |
| $2^{nd}$ line from concentration unit (water-rich fraction) | Phenol (wt %) | 24.07 | 23.73 |
| | Acetone (wt %) | 0.60 | 1.97 |
| | Methanol (ppm) | 60 | 197 |
| | Water (wt %) | balance | balance |
| Bottom recirculation part | Phenol (wt %) | 5.87 | 6.06 |
| | Sodium phenoxide (wt %) | 1.81 | 1.78 |
| | Methanol (ppm) | 50 | 50 |
| | Hydroxy acetone (wt %) | 0.11 | 0.11 |
| | Water (wt %) | balance | balance |
| Content of methanol in bottom recirculation part of removal column (ppm) | | 50 | 50 |
| Methanol removal rate (%) | | 95 | 95 |
| Amount of energy consumption (heat duty) (G cal/hr) | | 1.05 | 1.08 |
| Reflux ratio | | 0.81 | 0.98 |

Referring to Table 1, methanol and acetone introduced from the first supply line 41 and the second supply line 42 are removed through the overhead in the removal column RC, and it can be confirmed that the content of methanol in the flow recirculated through the bottom is 50 ppm and less, and 95% of methanol can be removed. In other words, it can be seen that methanol, which requires high energy consumption and has poor removal efficiency when removed, may be removed at a high removal rate, and energy consumption may also be reduced.

Accordingly, the production system of phenol and bisphenol A to which the removal unit according to the presentation is applied is capable of improving the lifespan of a catalyst of a reactor by continuously and efficiently removing methanol included in acetone, and of controlling the content of acetone regardless of the capacity of a dehydration column, thereby easily controlling the selectivity of bisphenol A.

Comparative Example

The same distillation tower used in Examples 1 and 2 was installed to remove methanol before the reaction of bisphenol A, that is in a flow in which a raw material flows into a reactor, and a simulation for a methanol removal process was performed. The composition in the acetone feed and the composition of the overhead and bottom flows of the methanol removal column are shown in Table 2 below.

TABLE 2

| Component | Feed | Top | Bottom |
|---|---|---|---|
| Methanol (wt %) | 0.02 | 0.19 | 0.01 |
| Acetaldehyde (ppm) | 0.04 | 0.73 | |
| Water (ppm) | 0.08 | 0.11 | 0.08 |
| Acetone (wt %) | balance | balance | balance |
| Methanol removal rate (%) | | 53 | |
| Reflux ratio | | 28.75 | |

Table 2 shows the result of a simulation for a case in which a column is installed to remove methanol before a raw material of acetone is introduced to a reactor in a production system of bisphenol A, which is a method conventionally applied. Referring to the result, it can be confirmed that since the removal rate of methanol is only 53%, unremoved methanol is introduced to a reactor of bisphenol A and causes a problem of deteriorating the lifespan of a catalyst unlike Examples 1 and 2. In addition, since the removal rate is not good as seen above, it is not possible to freely control the content of acetone so that it is difficult to achieve the improvement of the lifespan of a catalyst and the selectivity of bisphenol A at the same time.

In addition, a reflux ratio is directly related to energy consumption, and as a reflux ratio increases, it means that energy consumption is significant. Referring to the reflux ratio above, since Example 1 has a significantly lower value of reflux ratio when compared with that of Comparative Example 1, it can be confirmed that the energy consumption thereof is small. From this, it can be seen that when the removal unit according to the present invention is applied, it is possible to remove most of methanol, and to reduce energy consumption.

While the present invention has been described in detail with reference to the preferred embodiments thereof, it is to be understood that the scope of the present invention is not limited thereto, and various modifications and improvements of those skilled in the art using the basic concept of the present invention as defined in the following claims are also intended to be included within the scope of the invention.

DESCRIPTION OF SYMBOLS

10: Purification unit
11: purification unit discharge part
12: First column inflow line
13: Acetone-rich discharge line
14: Acetone removal discharge line
15: Aqueous layer-rich discharge line
16: Phenol-rich discharge line
17: Low melting point substance removal line
18: Acetone discharge line
19: Organic layer discharge line
20: Concentration unit
21: Dehydration column inflow line
22: Unreacted acetone discharge line
24: Acetone recovery column overhead discharge line
25: Dehydration column bottom discharge line
26: Water-rich discharge line
30, 40: Removal unit
31: Purification unit discharge part
32: Concentration unit discharge part
33: Overhead purge part
34: Bottom recirculation part
41: First supply line
42: Second supply line
43: First dephenolation process inflow line
44: Second dephenolation process inflow line
C1: First column C2: Second column
Sp: Separator N: Neutralizer
DH: Dehydration column
Ar: Acetone recovery column
FS: Flash unit
RC: Removal column

The invention claimed is:

1. A system for producing phenol and bisphenol A comprising:
a first production unit for producing phenol comprising a decomposition reaction unit and a purification unit;
a second production unit for producing bisphenol A comprising a reaction unit and a concentration unit; and
a removal unit for removing methanol and acetone during the production of phenol and bisphenol A the removal unit comprising:
a removal column comprising an overhead purge part, a bottom recirculation part and a supply part;
wherein the supply part comprises a purification unit discharge part to supply methanol, acetone, and water discharged from the purification unit to the removal column and a concentration unit discharge part to supply phenol, acetone, and water discharged from the concentration unit to the removal column,
wherein the supply part is provided to the midsection of the removal column;
wherein the overhead purge part removes methanol and acetone from the removal column; and
wherein the bottom recirculation part recirculates phenol, water, and trace amounts of methanol and acetone to the purification unit.

2. The system for producing phenol and bisphenol A according to claim 1,
wherein the purification unit comprises:
a first column for separating a reaction product discharged from the decomposition reaction unit into an acetone-rich fraction and a phenol-rich fraction;
a second column connected to an acetone-rich discharge line for purifying the acetone-rich fraction discharged from a top of the first column; and
a separator connected to the acetone removal discharge line for separating an acetone removal fraction discharged from the bottom of the second column into an aqueous layer fraction comprising methanol, acetone and water, and an organic layer fraction, and
wherein the purification unit discharge part comprises an aqueous layer discharge line through which the aqueous layer fraction is discharged from the separator.

3. The system for producing phenol and bisphenol A according to claim 1,
wherein the concentration unit comprises:
a dehydration column for removing unreacted acetone and water from a reaction product discharged from the reaction unit; and
an acetone recovery column connected to an unreacted acetone discharge line discharged from an upper end of the dehydration column for recovering acetone by removing acetone from the water-rich fraction, and
wherein the concentration unit discharge part comprises a water-rich discharge line through which a water-rich fraction comprising phenol, acetone, and water is discharged from the acetone recovery column.

4. The system for producing phenol and bisphenol A according to claim 1, wherein the bottom recirculation part recirculated to the purification unit comprises methanol in an amount of 100 ppm or less based on a total weight of flow.

5. The system for producing phenol and bisphenol A according to claim 1, wherein a reaction in which phenol and acetone are produced from cumene oxide and an acid solution is performed in the decomposition reaction unit.

6. The system for producing phenol and bisphenol A according to claim 2, wherein the purification unit further comprises a neutralizer at a front end part of the first column, and the neutralizer neutralizes the reaction product discharged from the decomposition reaction unit.

7. The system for producing phenol and bisphenol A according to claim 1, wherein a reaction in which bisphenol A and water are produced is performed in the reaction unit.

\* \* \* \* \*